United States Patent [19]
Coleman et al.

[11] Patent Number: 6,066,488
[45] Date of Patent: May 23, 2000

[54] CATHEPSIN C HOMOLOG

[75] Inventors: Roger Coleman, Mountain View; Scott Michael Braxton, San Mateo; Jeffrey J. Seilhamer, Los Altos Hills, all of Calif.

[73] Assignee: Incyte Pharmaceuticals, Inc., Palo Alto, Calif.

[21] Appl. No.: 08/871,314

[22] Filed: Jun. 9, 1997

Related U.S. Application Data

[62] Division of application No. 08/426,428, Apr. 19, 1995, Pat. No. 5,637,462.
[51] Int. Cl.$^7$ .............................. C12N 9/48; C12N 9/50; C12N 9/64; C12N 15/00
[52] U.S. Cl. .................. 435/212; 435/219; 435/226; 435/325; 424/94.63; 424/94.65; 530/412; 536/23.2; 536/23.1; 536/320.1
[58] Field of Search ................... 435/212, 69.1, 435/219, 226, 325; 424/94.63, 94.65; 530/412; 536/23.2, 23.1, 320.1

[56] References Cited

U.S. PATENT DOCUMENTS 5,366,862  11/1994  Venton et al. ........................ 435/7.1

FOREIGN PATENT DOCUMENTS

WO 93/24634  12/1993  WIPO .

OTHER PUBLICATIONS

Tsuchiya et al., "Establishment and Characterization of a Human Acute Monocytic Leukemia Cell Line (THP–1)" *Int J Cancer* 26:171–176 (1980).

Auwerx, J., "The human leukemia cell line, THP–1: A multifacetted model for the study of monocyte–macrophage differentiation" *Experientia* 47:22–28 (1991).

Cochran et al., "Regulation of interleuikin–1β and tumor necrosis factor secretion by the human monocytic leukemia cell line, THP–1" *Agents and Actions* 27:271–273 (1989).

Kominami et al., "The Primary Structure and Tissue Distribution of Cathepsin C" *Biol Chem* 373:367–373 (1992).

Kuribayashi et al., "Endopeptidase Activity of Cathepsin C, Dipeptidyl Aminopeptidase I, from Bovine Spleen" *J Biochem* 113:441–449 (1993).

Muno et al., "Processing and Transport of the Precursor of Cathepsin C during Its Transfer into Lysosomes" *Arch Biochem Biophy* 396:103–110 (1993).

Tezuka et al., "Molecular cloning of a possible cysteine proteinase predominantly expressed in osteoclasts" Abstract available only, *J Biol Chem* 269 (2) :1106–1109 (1994).

Ishidoh et al., "Molecular Cloning of cDNA for Rat Cathepsin C" *J. Biol. Chem.* 266 (25) :16312–16317 (1991).

Paris et al., "Molecular cloning and sequence analysis of human preprocathepsin C" *FEBS Lett* 369:326–330 (1995).

Dolenc et al., "Oligomeric structure and substrate induced inhibition of human cathepsin C" *J. Biol. Chem.* 270 (37) :21626–21631 (1995).

McGuire, M. et al., Arch. Biochem. Biophys., vol. 295, No. 2, pp. 280–288, 1992.

*Primary Examiner*—Lisa J. Hobbs
*Assistant Examiner*—Peter P. Tung
*Attorney, Agent, or Firm*—Diana Hamlet-Cox; Incyte Pharmaceuticals, Inc.

[57]  ABSTRACT

The present invention provides nucleotide and amino acid sequences that identify and encode a new cathepsin C homolog (RCP) expressed in THP-1 cells. The present invention also provides for antisense molecules to the nucleotide sequences which encode RCP, expression vectors for the production of purified RCP, antibodies capable of binding specifically to RCP, hybridization probes or oligonucleotides for the detection of RCP-encoding nucleotide sequences, genetically engineered host cells for the expression of RCP, diagnostic tests for activation of monocyte/macrophages based on RCP-encoding nucleic acid molecules, and use of the protein to produce antibodies capable of binding specifically to the protein and use of the protein to screen for inhibitors.

4 Claims, 6 Drawing Sheets

```
                        9                18               27               36               45               54
5' ATG GGT GCT GGG CCC TCC TTG CTG CTC GCC GCC CTC CTG CTG CTT CTC TCC GGC
   Met Gly Ala Gly Pro Ser Leu Leu Leu Ala Ala Leu Leu Leu Leu Leu Ser Gly 63                72               81               90               99              108
   GAC GGC GCC GTG CGC TGC GAC ACA CCT GCC AAC TGC ACC TAT CTT GAC CTG CTG
   Asp Gly Ala Val Arg Cys Asp Thr Pro Ala Asn Cys Thr Tyr Leu Asp Leu Leu 117               126              135              144              153              162
   GGC ACC TGG GTC TTC CAG GTG GGC TCC AGC GGT TCC CAG CGC GAT GTC AAC TGC
   Gly Thr Trp Val Phe Gln Val Gly Ser Ser Gly Ser Gln Arg Asp Val Asn Cys 171               180              189              198              207              216
   TCG GTT ATG GGA CCA CAA GAA AAA AAA GTA GTG GTG TAC CTT CAG AAG CTG GAT
   Ser Val Met Gly Pro Gln Glu Lys Lys Val Val Val Tyr Leu Gln Lys Leu Asp 225               234              243              252              261              270
   ACA GCA TAT GAT GAC CTT GGC AAT TCT GGC CAT TTC ACC ATC ATT TAC AAC CAA
   Thr Ala Tyr Asp Asp Leu Gly Asn Ser Gly His Phe Thr Ile Ile Tyr Asn Gln 279               288              297              306              315              324
   GGC TTT GAG ATT GTG TTG AAT GAC TAC AAG TGG TTT GCC TTT TTT AAG TAT AAA
   Gly Phe Glu Ile Val Leu Asn Asp Tyr Lys Trp Phe Ala Phe Phe Lys Tyr Lys 333               342              351              360              369              378
   GAA GAG GGC AGC AAG GTG ACC ACT TAC TGC AAC GAG ACA ATG ACT GGG TGG GTG
   Glu Glu Gly Ser Lys Val Thr Thr Tyr Cys Asn Glu Thr Met Thr Gly Trp Val 387               396              405              414              423              432
   CAT GAT GTG TTG GGC CGG AAC TGG GCT TGT TTC ACC GGA AAG AAG GTG GGA ACT
   His Asp Val Leu Gly Arg Asn Trp Ala Cys Phe Thr Gly Lys Lys Val Gly Thr 441               450              459              468              477              486
   GCC TCT GAG AAT GTG TAT GTC AAC ACA GCA CAC CTT AAG AAT TCT CAG GAA AAG
   Ala Ser Glu Asn Val Tyr Val Asn Thr Ala His Leu Lys Asn Ser Gln Glu Lys 495               504              513              522              531              540
   TAT TCT AAT AGG CTC TAC AAG TAT GAT CAC AAC TTT GTG AAA GCT ATC AAT GCC
   Tyr Ser Asn Arg Leu Tyr Lys Tyr Asp His Asn Phe Val Lys Ala Ile Asn Ala 549               558              567              576              585              594
   ATT CAG AAG TCT TGG ACT GCA ACT ACA TAC ATG GAA TAT GAG ACT CTT ACC CTG
   Ile Gln Lys Ser Trp Thr Ala Thr Thr Tyr Met Glu Tyr Glu Thr Leu Thr Leu 603               612              621              630              639              648
   GGA GAT ATG ATT AGG AGA AGT GGT GGC CAC AGT CGA AAA ATC CCA AGG CCC AAA
   Gly Asp Met Ile Arg Arg Ser Gly Gly His Ser Arg Lys Ile Pro Arg Pro Lys 657               666              675              684              693              702
   CCT GCA CCA CTG ACT GCT GAA ATA CAG CAA AAG ATT TTG CAT TTG CCA ACA TCT
   Pro Ala Pro Leu Thr Ala Glu Ile Gln Gln Lys Ile Leu His Leu Pro Thr Ser
```

FIG. 1A

```
      711           720           729           738           747           756
TGG GAC TGG AGA AAT GTT CAT GGT ATC AAT TTT GTC AGT CCT GTT CGA AAC CAA
Trp Asp Trp Arg Asn Val His Gly Ile Asn Phe Val Ser Pro Val Arg Asn Gln 765           774           783           792           801           810
GCA TCC TGT GGC AGC TGC TAC TCA TTT GCT TCT ATG GGT ATG CTA GAA GCG AGA
Ala Ser Cys Gly Ser Cys Tyr Ser Phe Ala Ser Met Gly Met Leu Glu Ala Arg 819           828           837           846           855           864
ATC CGT ATA CTA ACC AAC AAT TCT CAG ACC CCA ATC CTA AGC CCT CAG GAG GTT
Ile Arg Ile Leu Thr Asn Asn Ser Gln Thr Pro Ile Leu Ser Pro Gln Glu Val 873           882           891           900           909           918
GTG TCT TGT AGC CAG TAT GCT CAA GGC TGT GAA GGC GGC TTC CCA TAC CTT ATT
Val Ser Cys Ser Gln Tyr Ala Gln Gly Cys Glu Gly Gly Phe Pro Tyr Leu Ile 927           936           945           954           963           972
GCA GGA AAG TAC GCC CAA GAT TTT GGG CTG GTG GAA GAA GCT TGC TTC CCC TAC
Ala Gly Lys Tyr Ala Gln Asp Phe Gly Leu Val Glu Glu Ala Cys Phe Pro Tyr 981           990           999           1008          1017          1026
ACA GGC ACT GAT TCT CCA TGC AAA ATG AAG GAA GAC TGC TTT CGT TAT TAC TCC
Thr Gly Thr Asp Ser Pro Cys Lys Met Lys Glu Asp Cys Phe Arg Tyr Tyr Ser 1035          1044          1053          1062          1071          1080
TCT GAG TAC CAC TAT GTA GGA GGT TTC TAT GGA GGC TGC AAT GAA GCC CTG ATG
Ser Glu Tyr His Tyr Val Gly Gly Phe Tyr Gly Gly Cys Asn Glu Ala Leu Met 1089          1098          1107          1116          1125          1134
AAG CTT GAG TTG GTC CAT CAT GGG CCC ATG GCA GTT GCT TTT GAA GTA TAT GAT
Lys Leu Glu Leu Val His His Gly Pro Met Ala Val Ala Phe Glu Val Tyr Asp 1143          1152          1161          1170          1179          1188
GAC TTC CTC CAC TAC AAA AAG GGG ATC TAC CAC CAC ACT GGT CTA AGA GAC CCT
Asp Phe Leu His Tyr Lys Lys Gly Ile Tyr His His Thr Gly Leu Arg Asp Pro 1197          1206          1215          1224          1233          1242
TTC AAC CCC TTT GAG CTG ACT AAT CAT GCT GTT CTG CTT GTG GGC TAT GGC ACT
Phe Asn Pro Phe Glu Leu Thr Asn His Ala Val Leu Leu Val Gly Tyr Gly Thr 1251          1260          1269          1278          1287          1296
GAC TCA GCC TCT GGG ATG GAT TAC TGG ATT GTT AAA AAC AGC TGG GGC ACC GGC
Asp Ser Ala Ser Gly Met Asp Tyr Trp Ile Val Lys Asn Ser Trp Gly Thr Gly 1305          1314          1323          1332          1341          1350
TGG GGT GAG AAT GGC TAC TTC CGG ATC CGC AGA GGA ACT GAT GAG TGT GCA ATT
Trp Gly Glu Asn Gly Tyr Phe Arg Ile Arg Arg Gly Thr Asp Glu Cys Ala Ile 1359          1368          1377          1386
GAG AGC ATA GCA GTG GCA GCC ACA CCA ATT CCT AAA TTG 3'
Glu Ser Ile Ala Val Ala Ala Thr Pro Ile Pro Lys Leu
```

FIG. 1B

```
         M G . . . . . L . A A L L L . L . G . . . V . . D T P A N C    CONSENSUS #1
         M G A G T S L L L A A L L L V L L G V G A V S S D T P A N C    MAJORITY
                         10                  20                  30
     1   M G A G P S L L L A A L L L L L S G D G A V R C D T P A N C    14284
     1   M G P W T H S L R A A L L L V L L G V C T V S S D T P A N C    RATCATC

T Y . D L L G T W V F Q V G . . . . . . . . . N C S V M . P .  CONSENSUS #1
         T Y L D L L G T W V F Q V G S S G S Q S D V N C S V M G P T    MAJORITY
                         40                  50                  60
    31   T Y L D L L G T W V F Q V G S S G S Q R D V N C S V M G P Q    14284
    31   T Y P D L L G T W V F Q V G P R H P R S H I N C S V M E P T    RATCATC

E . K V V . . L . K L D T A Y D . . G N S G . F T . I Y N Q    CONSENSUS #1
         E E K V V V H L Q K L D T A Y D D V G N S G H F T L I Y N Q    MAJORITY
                         70                  80                  90
    61   E K V V V Y L Q K L D T A Y D D L G N S G H F T I I Y N Q      14284
    61   E E K V V I H L K K L D T A Y D E V G N S G Y F T L I Y N Q    RATCATC

G F E I V L N D Y K W F A F F K Y . . . G S . . . . Y C . E    CONSENSUS #1
         G F E I V L N D Y K W F A F F K Y E V E G S K A I S Y C N E    MAJORITY
                        100                 110                 120
    91   G F E I V L N D Y K W F A F F K Y K E E G S K V T T Y C N E    14284
    91   G F E I V L N D Y K W F A F F K Y E V K G S R A I S Y C H E    RATCATC

T M T G W V H D V L G R N W A C F . G K K . . . . S E . V Y    CONSENSUS #1
         T M T G W V H D V L G R N W A C F V G K K V G T A S E N V Y    MAJORITY
                        130                 140                 150
   121   T M T G W V H D V L G R N W A C F T G K K V G T A S E N V Y    14284
   121   T M T G W V H D V L G R N W A C F V G K K M A N H S E K V Y    RATCATC

V N . A H L . . . Q E K Y S . R L Y . . . H N F V K A I N .    CONSENSUS #1
         V N V A H L G G L Q E K Y S E R L Y S H D H N F V K A I N A    MAJORITY
                        160                 170                 180
   151   V N T A H L K N S Q E K Y S N R L Y K Y D H N F V K A I N A    14284
   151   V N V A H L G G L Q E K Y S E R L Y S H N H N F V K A I N S    RATCATC
```

FIG. 2A

```
         . Q K S W T A T T Y . E Y E . L . . . D . I R R S G . H S .     CONSENSUS #1
         V Q K S W T A T T Y E E Y E T L S L G D L I R R S G G H S G     MAJORITY
                     190             200             210
     181 I Q K S W T A T T Y M E Y E T L T L G D M I R R S G G H S R     14284
     181 V Q K S W T A T T Y E E Y E K L S I R D L I R R S G - H S G     RATCATC

. I . R P K P A P . T . E I Q Q . I L . L P . S W D W R N V     CONSENSUS #1
         K I L R P K P A P L T A E I Q Q Q I L S L P T S W D W R N V     MAJORITY
                     220             230             240
     211 K I P R P K P A P L T A E I Q Q K I L H L P T S W D W R N V     14284
     210 R I L R P K P A P I T D E I Q Q Q I L S L P E S W D W R N V     RATCATC

. G I N F V S P V R N Q . S C G S C Y S F A S . G M L E A R     CONSENSUS #1
         H G I N F V S P V R N Q A S C G S C Y S F A S L G M L E A R     MAJORITY
                     250             260             270
     241 H G I N F V S P V R N Q A S C G S C Y S F A S M G M L E A R     14284
     240 R G I N F V S P V R N Q E S C G S C Y S F A S L G M L E A R     RATCATC

I R I L T N N S Q T P I L S P Q E V V S C S . Y A Q G C . G     CONSENSUS #1
         I R I L T N N S Q T P I L S P Q E V V S C S Q Y A Q G C D G     MAJORITY
                     280             290             300
     271 I R I L T N N S Q T P I L S P Q E V V S C S Q Y A Q G C E G     14284
     270 I R I L T N N S Q T P I L S P Q E V V S C S P Y A Q G C D G     RATCATC

G F P Y L I A G K Y A Q D F G . V E E . C F P Y T . T D . P     CONSENSUS #1
         G F P Y L I A G K Y A Q D F G V V E E A C F P Y T G T D A P     MAJORITY
                     310             320             330
     301 G F P Y L I A G K Y A Q D F G L V E E A C F P Y T G T D S P     14284
     300 G F P Y L I A G K Y A Q D F G V V E E N C F P Y T A T D A P     RATCATC

C K . K E . C . R Y Y S S E Y . Y V G G F Y G G C N E A L M     CONSENSUS #1
         C K M K E D C L R Y Y S S E Y H Y V G G F Y G G C N E A L M     MAJORITY
                     340             350             360
     331 C K M K E D C F R Y Y S S E Y H Y V G G F Y G G C N E A L M     14284
     330 C K P K E N C L R Y Y S S E Y Y Y V G G F Y G G C N E A L M     RATCATC
```

FIG. 2B

```
            K L E L V . H G P M A V A F E V . D D F L H Y . . G I Y H H      CONSENSUS #1
            K L E L V K H G P M A V A F E V H D D F L H Y K S G I Y H H      MAJORITY
                              370               380              390
      361   K L E L V|H|H G P M A V A F E V|Y|D D F L H Y|K K|G I Y H H      14284
      360   K L E L V|K|H G P M A V A F E V|H|D D F L H Y|H S|G I Y H H      RATCATC

T G L . D P F N P F E L T N H A V L L V G Y G . D . . . G .      CONSENSUS #1
            T G L S D P F N P F E L T N H A V L L V G Y G T D S A S G L      MAJORITY
                              400               410              420
      391   T G L|R|D P F N P F E L T N H A V L L V G Y G|T|D S A S|G M|    14284
      390   T G L|S|D P F N P F E L T N H A V L L V G Y G|K|D P V T|G L|    RATCATC

D Y W I V K N S W G . . W G E . G Y F R I R R G T D E C A I      CONSENSUS #1
            D Y W I V K N S W G S G W G E S G Y F R I R R G T D E C A I      MAJORITY
                              430               440              450
      421   D Y W I V K N S W G|T G|W G E|N|G Y F R I R R G T D E C A I      14284
      420   D Y W I V K N S W G|S Q|W G E|S|G Y F R I R R G T D E C A I      RATCATC

E S I A . A A . P I P K L                                        CONSENSUS #1
            E S I A V A A I P I P K L                                        MAJORITY
                              460
      451   E S I A|V A A T|P I P K L                                        14284
      450   E S I A|M A A I|P I P K L                                        RATCATC
```

CATHEPSIN C HOMOLOG

The present U.S. utility patent application is a divisional application of then U.S. Ser. No. 08/426,428, filed Apr. 19, 1995, now U.S. Pat. No. 5,637,462, from which priority is claimed.

FIELD OF THE INVENTION

The present invention is in the field of molecular biology; more particularly, the present invention describes the nucleic acid and amino acid sequences of a novel cathepsin C homolog derived from activated THP-1 cells.

BACKGROUND OF THE INVENTION
THP-1 Cells

THP-1 is a human leukemic cell line with distinct monocytic characteristics derived from the blood of a 1-year-old boy with acute monocytic leukemia (Tsuchiya S et al (1980) Int J Cancer 26:171–176). The monocytic nature of THP-1 was established using the following cytological and cytochemical criteria: 1) a-naphthyl butyrate esterase activity which could be inhibited by NaF (sodium fluoride), 2) production of lysozyme, 3) phagocytosis (the engulfing of extracellular materials) of latex particles and sensitized sheep red blood cells, and 4) ability of mitomycin C-treated THP-1 cells to activate T-lymphocytes following concanavalin A treatment. Morphologically, the cytoplasm contained small azurophilic granules, the nucleus was indented and irregularly shaped with deep folds, and the cell membrane had Fc and C3b receptors which probably function in phagocytosis.

Typical monocytes develop from monoblasts through promonocytes in the bone marrow and in their mature form have a half-life of approximately three days. Roughly 75% of the circulating monocyte pool is found along the walls of blood vessels although these cells randomly migrate into tissues and become antigen-presenting or phagocytic. Antigen-presenting monocytes include interdigitating reticular and follicular dendritic cells of the lymph nodes and skin. Phagocytic monocytes are prominent as Kupffer cells of the liver and in the lung alveoli and bone marrow.

Whereas precursor monocytes are rich in azurophilic, peroxidase-containing cytoplasmic granules, macrophages have more numerous cell surface receptors by which they monitor their environment. These include receptors for immunoglobulin, complement, growth factors, lipoproteins, peptides and polysaccharides. Binding of ligands to these receptors triggers macrophage proliferation, chemotaxis, secretion and phagocytosis.

Many human myeloid and myelomonocytic cell lines retain some ability to differentiate into more mature phenotypes in response to various internal stimuli including growth factors, lymphokines, cytokines, vitamin D derivatives, and tumor promoters and external agents such as trauma, smoking, UV irradiation, asbestos exposure, and steroids. THP-1 cells treated with the tumor promoter 12-O-tetradecanoyl-phorbol-13 acetate (TPA) are induced to stop proliferating and differentiate into macrophage-like cells which mimic native monocyte-derived macrophages both morphologically and physiologically.

These monocyte/macrophage-like cells exhibit changes in gene expression such as the coinduction of C-fos, c-jun and the down-regulation of c-myb (Auwerx J (1991) Experientia 47:22–31), increase in density of the complement C3b receptor, and decrease in both FcR and the adhesion molecule, CD4. In addition, THP-1 cells produce lipoprotein lipase and apolipoprotein E, associated with atherosclerotic lesions, secrete several proinflammatory cytokines, including IL-1β and TNF (Cochran F R and Finch-Arietta M B (1989) Agents and Actions 27:271–273), and may elaborate powerful oxidants and tissue destroying proteases, such as the cathepsins.

A new human cysteine protease, a cathepsin C homolog (Incyte Clone 14284), has been identified among the up-regulated genes from activated THP-1 cells. It is an acidic, lysosomal dipeptidyl aminopeptidase and has 79.3% amino acid sequence identity with rat cathepsin C isolated as a rat kidney cDNA (Kominami E et al (1992) Biol Chem 373:367–73). Incyte 14284 has the conserved residues—cys at 258, his at 405, and asn at 427—of the catalytic triad and the NNS glycosylation site in the hydrophobic region which are common to the cysteine proteases.

Kominami et al (supra) reported the presence of rat cathepsin C mRNA in almost all rat tissues. Large amounts of transcript were prevalent in liver, spleen, small and large intestine, lung and kidney, moderate amounts in esophagus, stomach, and heart, and small amounts in brain, pancreas, adrenal gland and testis. Transcript prevalence appears to correlate with the expected presence and activity of monocyte/macrophages in normal tissue function.

Cultured macrophages have been used to study the processing of cathepsin C from its synthesis as a propeptide to the mature oligomeric enzyme. Both precursor and mature cathepsin C are phosphorylated and glycosylated, and it appears that oligomerization occurs prior to entry into the lysosome (Muno D et al (1993) Arch Biochem Biophy 306:103– 10). In studies utilizing synthetic substrates, cathepsin C was shown to function as an endopeptidase in intracellular protein degradation and as an exopeptidase (dipeptidyl aminopeptidase) in cell growth and neuraminidase activation (Kuribayashi M et al (1993) J Biochem 113:441–49).

In the normal synovium, monocytes give rise to osteoclasts which are giant, multi-nuclear cells (Tezuka K-I et al. 1994 J Biol Chem 269: 1106–1109) which attach to the bone surface. These cells produce an acidic microenvironment in which minerals and organic components of the bone matrix are solubilized. Adult bone mass generally remains constant because the rates of bone deposition and absorption are equal; however, in rheumatoid arthritis, the number and activity of osteoclasts increase under the influence of growth factors and tumor promoters. Among other hydrolases, osteoclasts produce cathepsin C which plays a role in degrading collagen, laminin, elastin and other structural proteins which comprise the extracellular matrix of the bones. Once the bone is weakened, it is even more susceptible to bone resorption, tumor invasion and metastasis.

Rheumatoid arthritis is just one example of a monocyte/macrophage disorder; in others, macrophages participate in other ways. For example, in arteriosclerosis, macrophages accumulate cholesterol from blood lipoproteins and become the foam cells of human atherosclerotic lesions. Renegade activated monocytes have also been implicated in defective defense against infection, bowel damage, osteoporosis, toxic shock syndrome, and systemic lupus erythematosus.

SUMMARY OF THE INVENTION

The subject invention provides a unique nucleotide sequence which encodes a novel human cathepsin C homolog, also known as rcp. The new gene, which was identified within Incyte Clone 14284, encodes RCP polypeptide, and represents a new human cysteine protease.

The invention also comprises diagnostic tests for physiologic or pathologic activity of activated monocytes or macrophages which include the steps of testing a sample or an extract thereof with rcp DNA, fragments or oligomers thereof. Further aspects of the invention include the antisense DNA of rcp; cloning or expression vectors containing rcp; host cells or organisms transformed with expression vectors containing rcp; a method for the production and recovery of purified RCP polypeptide from host cells; purified RCP polypeptide; antibodies and inhibitors to RCP, and pharmacological compounds using RCP antibodies.

DESCRIPTION OF THE FIGURES

FIG. 1 displays the nucleotide sequence for rcp and the predicted amino acid sequence of RCP polypeptide.

DETAILED DESCRIPTION OF THE INVENTION

Definitions

As used herein, human cathepsin C refers to an RCP polypeptide, naturally occurring RCP polypeptide, or active fragments thereof, which are encoded by mRNAs transcribed from the cDNA of Seq ID No 1.

"Active" refers to those forms of RCP which retain biologic and/or immunologic activities of any naturally occurring RCP.

"Naturally occurring RCP" refers to RCP produced by human cells that have not been genetically engineered and specifically contemplates various RCPs arising from post-translational modifications of the polypeptide including but not limited to acetylation, carboxylation, glycosylation, phosphorylation, lipidation and acylation.

"Derivative" refers to polypeptides derived from naturally occurring RCP by chemical modifications such as ubiquitination, labeling (e.g., with radionuclides, various enzymes, etc.), pegylation (derivatization with polyethylene glycol), or by insertion (or substitution by chemical synthesis) of amino acids (aa) such as ornithine, which do not normally occur in human proteins.

"Recombinant variant" refers to any polypeptide differing from naturally occurring RCP by aa insertions, deletions, and substitutions, created using recombinant DNA techniques. Guidance in determining which aa residues may be replaced, added or deleted without abolishing activities of interest, such as cell adhesion and chemotaxis, may be found by comparing the sequence of the particular RCP with that of homologous cathepsins and minimizing the number of aa sequence changes made in regions of high homology.

Preferably, aa "substitutions" are the result of replacing one aa with another aa having similar structural and/or chemical properties, such as the replacement of a leucine with an isoleucine or valine, an aspartate with a glutamate, or a threonine with a serine, i.e., conservative aa replacements. "Insertions" or "deletions" are typically in the range of about 1 to 5 aa. The variation allowed may be experimentally determined by systematically making insertions, deletions, or substitutions of aa in an RCP molecule using recombinant DNA techniques and assaying the resulting recombinant variants for activity.

Where desired, a "signal or leader sequence" can direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of aa residues of at least about 5 aa, often at least about 7 aa, typically at least about 9 to 13 aa, and, in various embodiments, at least about 17 or more aa. To be active, any RCP polypeptide must have sufficient length to display biologic and/or immunologic activity on their own or when conjugated to a carrier protein such as keyhole limpet hemocyanin.

An "oligonucleotide" or polynucleotide "fragment", "portion," or "segment" is a stretch of nucleotide residues which is long enough to use in polymerase chain reaction (PCR) or various hybridization procedures to amplify or simply reveal related parts of mRNA or DNA molecules. One or both oligonucleotide probes will comprise sequence that is identical or complementary to a portion of rcp where there is little or no identity or complementarity with any known or prior art molecule. The oligonucleotide probes will generally comprise between about 10 nucleotides and 50 nucleotides, and preferably between about 15 nucleotides and about 30 nucleotides.

"Activated monocytes" as used herein refers to the activated, mature monocytes or macrophages found in immunologically active tissues.

"Monocyte/macrophage" disorders" include but are not limited to arteriosclerosis, leukemia, systemic lupus erythematosus, osteoporosis, rheumatoid arthritis, and toxic shock syndrome.

"Animal" as used herein may be defined to include human, domestic or agricultural (cats, dogs, cows, sheep, etc) or test species (mouse, rat, rabbit, etc).

The present invention includes purified RCP polypeptides from natural or recombinant sources, cells transformed with recombinant nucleic acid molecules encoding RCP. Various methods for the isolation of the RCP polypeptides may be accomplished by procedures well known in the art. For example, such polypeptides may be purified by immunoaffinity chromatography by employing the antibodies provided by the present invention. Various other methods of protein purification well known in the art include those described in Deutscher M (1990) Methods in Enzymology, Vol 182, Academic Press, San Diego Calif.; and Scopes R (1982) Protein Purification: Principles and Practice. Springer-Verlag, New York City, both incorporated herein by reference.

"Recombinant" may also refer to a polynucleotide which encodes RCP and is prepared using recombinant DNA techniques. The DNAs which encode RCP may also include allelic or recombinant variants and mutants thereof.

"Nucleic acid probes" are prepared based on the cDNA sequences which encode RCP provided by the present invention. Nucleic acid probes comprise portions of the sequence having fewer nucleotides than about 6 kb, usually fewer than about 1 kb. After appropriate testing to eliminate false positives, these probes may be used to determine whether mRNAs encoding RCP are present in a cell or tissue or to isolate similar nucleic acid sequences from chromosomal DNA extracted from such cells or tissues as described by Walsh P S et al (1992, PCR Methods Appl 1:241–250).

Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, Cold Spring Harbor Laboratory, Cold Spring Harbor N.Y.; or Ausubel FM et al (1989) Current Protocols in Molecular Biology, John Wiley & Sons, New York City, both incorporated herein by reference.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide, including but not limited to ligand-binding affinities, interchain affinities, or polypeptide degradation or turnover rate. One example involves inserting a stop codon into the nucleotide sequence to limit the size of RCP so as to provide a binding, non-activating ligand of smaller molecular weight which would serve to block the activity of the natural cathepsin C.

Detailed Description of the Invention

The present invention provides a nucleotide sequence found within Incyte 14284 uniquely identifying a new, human cathepsin C (RCP) of the cysteine protease family which is highly expressed in THP-1 cells. Because RCP is specifically expressed in activated monocytes, the nucleic acids (rcp), polypeptides (RCP) and antibodies to RCP are useful in diagnostic assays based on production of cathepsin C in cases of inflammation or disease. Excessive expression of RCP may lead to tissue damage or destruction. Therefore, a diagnostic test for RCP can accelerate diagnosis and proper treatment of monocyte/macrophage disorders including arteriosclerosis, leukemia, systemic lupus erythematosus, osteoporosis, rheumatoid arthritis, toxic shock syndrome and similar physiologic/pathologic problems.

The nucleotide sequences encoding RCP (or their complement) have numerous applications in techniques known to those skilled in the art of molecular biology. These techniques include use as hybridization probes, use in the construction of oligomers for PCR, use for chromosome and gene mapping, use in the recombinant production of RCP, and use in generation of anti-sense DNA or RNA, their chemical analogs and the like. Uses of nucleotides encoding RCP disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of RCP-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring rcp, and all such variations are to be considered as being specifically disclosed.

Although the nucleotide sequences which encode RCP and/or its variants are preferably capable of hybridizing to the nucleotide sequence of the naturally occurring rcp under stringent conditions, it may be advantageous to produce nucleotide sequences encoding RCP or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding RCP and/or its derivatives without altering the encoded aa sequence include the production of RNA transcripts having more desirable properties, such as a greater half-life, than transcripts produced from the naturally occurring sequence.

Nucleotide sequences encoding RCP may be joined to a variety of other nucleotide sequences by means of well established recombinant DNA techniques (cf Sambrook J et al. supra). Useful nucleotide sequences for joining to rcp include an assortment of cloning vectors, e.g., plasmids, cosmids, lambda phage derivatives, phagemids, and the like, that are well known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for rcp-specific nucleic acid hybridization probes capable of hybridizing with naturally occurring nucleotide sequences encoding RCP. Such probes may also be used for the detection of similar cathepsin C encoding sequences and should preferably contain at least 50% of the nucleotides from the conserved region or active site. The hybridization probes of the subject invention may be derived from the nucleotide sequences of the SEQ ID NO 1 or from genomic sequences including promoters, enhancer elements and/or possible introns of the respective naturally occurring rcps. Hybridization probes may be labeled by a variety of reporter groups, including radionuclides such as 32P or 35S, or enzymatic labels such as alkaline phosphatase coupled to the probe via avidin/biotin coupling systems, and the like.

PCR as described U.S. Pat. Nos 4,683,195; 4,800,195; and 4,965,188 provides additional uses for oligonucleotides based upon the nucleotide sequence which encodes RCP. Such probes used in PCR may be of recombinant origin, may be chemically synthesized, or a mixture of both and comprise a discrete nucleotide sequence for diagnostic use or a degenerate pool of possible sequences for identification of closely related genomic sequences.

Other means of producing specific hybridization probes for rcp DNAs include the cloning of nucleic acid sequences encoding RCP or RCP derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding RCP and their derivatives entirely by synthetic chemistry, after which the gene can be inserted into any of the many available DNA vectors using reagents, vectors and cells that are known in the art at the time of the filing of this application. Moreover, synthetic chemistry may be used to introduce mutations into the rcp sequences or any portion thereof.

The nucleotide sequence can be used in an assay to detect inflammation or disease associated with abnormal levels of expression of RCP. The nucleotide sequence can be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye is significantly elevated, the nucleotide sequence has hybridized with the sample, and the assay indicates the presence of inflammation and/or disease.

The nucleotide sequence for rcp can be used to construct hybridization probes for mapping that gene. The nucleotide sequence provided herein may be mapped to a particular chromosome or to specific regions of that chromosome using well known genetic and/or chromosomal mapping techniques. These techniques include in situ hybridization, linkage analysis against known chromosomal markers, hybridization screening with libraries, flow-sorted chromosomal preparations, or artificial chromosome constructions YAC or P1 constructions. The technique of fluorescent in situ hybridization of chromosome spreads has been described, among other places, in Verma et al (1988) Human Chromosomes: A Manual of Basic Techniques, Pergamon Press, New York City.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of rcp on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

Nucleotide sequences encoding RCP may be used to produce purified RCP using well known methods of recombinant DNA technology. Among the many publications that teach methods for the expression of genes after they have been isolated is Goeddel (1990) Gene Expression Technology, Methods and Enzymology, Vol 185, Academic Press, San Diego Calif. RCP may be expressed in a variety of host cells, either prokaryotic or eukaryotic. Host cells may be from the same species in which rcp nucleotide sequences are endogenous or from a different species. Advantages of producing RCP by recombinant DNA technology include obtaining adequate amounts of the protein for purification and the availability of simplified purification procedures.

Cells transformed with DNA encoding RCP may be cultured under conditions suitable for the expression of cathepsin C and recovery of the protein from the cell culture. RCP produced by a recombinant cell may be secreted or may be contained intracellularly, depending on the RCP sequence and the genetic construction used. In general, it is more convenient to prepare recombinant proteins in secreted form. Purification steps vary with the production process and the particular protein produced.

In addition to recombinant production, fragments of RCP may be produced by direct peptide synthesis using solid-phase techniques (cf Stewart et al (1969) Solid-Phase Peptide Synthesis, WH Freeman Co, San Francisco Calif.; Merrifield J (1963) J Am Chem Soc 85:2149–2154. In vitro protein synthesis may be performed using manual techniques or by automation. Automated synthesis may be achieved, for example, using Applied Biosystems 431A Peptide Synthesizer (Foster City, Calif. Calif.) in accordance with the instructions provided by the manufacturer. Various fragments of RCP may be chemically synthesized separately and combined using chemical methods to produce the full length molecule.

RCP for antibody induction does not require biological activity; however, the protein must be immunogenic. Peptides used to induce specific antibodies may have an aa sequence consisting of at least five aa, preferably at least 10 aa. They should mimic a portion of the aa sequence of the protein and may contain the entire aa sequence of a small naturally occurring molecule such as RCP. Short stretches of RCP aa may be fused with those of another protein such as keyhole limpet hemocyanin and the chimeric molecule used for antibody production.

Antibodies specific for RCP may be produced by inoculation of an appropriate animal with the polypeptide or an antigenic fragment. An antibody is specific for RCP if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R et al (1989) PNAS 86:3833–3837, or Huse W D et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding RCPs.

An additional embodiment of the subject invention is the use of RCP specific antibodies, inhibitors, receptors or their analogs as bioactive agents to treat monocyte/macrophage disorders including arteriosclerosis, leukemia, systemic lupus erythematosus, osteoporosis, rheumatoid arthritis, toxic shock syndrome and similar physiologic/pathologic problems.

Bioactive compositions comprising agonists, antagonists, receptors or inhibitors of RCP may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving RCP production and function.

The examples below are provided to illustrate the subject invention. These examples are provided by way of illustration and are not included for the purpose of limiting the invention.

EXAMPLES

I Isolation of mRNA and Construction of cDNA Libraries

The rcp sequence was identified among the sequences comprising the human THP-1 library. THP-1 is a human leukemic cell line derived from the blood of a 1-year-old boy with acute monocytic leukemia. Cells used for the PMA+ LPS library were cultured for 48 hr with 100 nm PMA in DMSO and for 4 hr with 1 µg/ml LPS. The THP-1 library was custom constructed by Stratagene (Stratagene, 11099 M. Torrey Pines Rd., La Jolla, Calif. 92037) essentially as described below.

Stratagene prepared the cDNA library using oligo d(T) priming. Synthetic adapter oligonucleotides were ligated onto the cDNA molecules enabling them to be inserted into the Uni-ZAP™ vector system (Stratagene). This allowed high efficiency unidirectional (sense orientation) lambda library construction and the convenience of a plasmid system with blue/white color selection to detect clones with cDNA insertions.

The quality of the cDNA library was screened using DNA probes, and then, the pBluescript® phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom-constructed library phage particles were infected into *E. coli* host strain XL1-Blue® (Stratagene). The high transformation efficiency of this bacterial strain increases the probability that the cDNA library will contain rare, under-represented clones. Alternative unidirectional vectors might include, but are not limited to, pcDNAI (Invitrogen, San Diego Calif.) and pSHIox-1 (Novagen, Madison Wis.).

II Isolation of cDNA Clones

The phagemid forms of individual cDNA clones were obtained by the in vivo excision process, in which XL1-BLUE was coinfected with an f1 helper phage. Proteins derived from both lambda phage and f1 helper phage initiated new DNA synthesis from defined sequences on the lambda target DNA and create a smaller, single-stranded circular phagemid DNA molecule that includes all DNA sequences of the pBluescript plasmid and the cDNA insert. The phagemid DNA was released from the cells and purified, then used to re-infect fresh bacterial host cells (SOLR, Stratagene Inc), where the double-stranded phagemid DNA was produced. Because the phagemid carries the gene for β-lactamase, the newly transformed bacteria were selected on medium containing ampicillin.

Phagemid DNA was purified using the QIAWELL-8 Plasmid Purification System from QIAGEN® DNA Purification System. This technique provides a rapid and reliable high-throughput method for lysing the bacterial cells and isolating highly purified phagemid DNA. The DNA eluted from the purification resin was suitable for DNA sequencing and other analytical manipulations.

III Sequencing of cDNA Clones

The cDNA inserts from random isolates of the THP-1 library were sequenced in part. Methods for DNA sequencing are well known in the art. Conventional enzymatic methods employed DNA polymerase Klenow fragment, SEQUENASE® (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 and the Applied Biosystems 377 or 373 DNA sequencer).

IV Homology Searching of cDNA Clones and Deduced Proteins

Each sequence so obtained was compared to sequences in GenBank using a search algorithm developed by Applied Biosystems Inc. and incorporated into the INHERIT™ 670 Sequence Analysis System. In this algorithm, Pattern Specification Language (developed by TRW Inc.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments of the protein sequence were used to display the results of the homology search.

After the initial identification of human cathepsin C among the THP-1 cDNAs, a search of the LIFESEQ™ database determined exact matches, the presence of rcp, in the following Incyte Clones: 1) Incyte 73566 and 76131, also in the THP-1 library; 2) Incyte 41151 in the T & B cell library; 3) Incyte 64728, 179782, and 179982 in the placenta library; 4) Incyte 78671, 78964, and 80537 in the rheumatoid synovium library; and 5) Incyte 82721 in the human umbilical vein endothelial cell library. The presence of rcp in these tissues is consistent with its expression in tissues with active immunological defenses, whether normal, inflamed, or diseased tissues, including those previously defined relative to monocyte/macrophage disorders.

Peptide and protein sequence homologies were ascertained using the INHERIT 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

The nucleotide and amino acid sequences for the entire coding region of the human cathepsin C homolog, RCP, claimed in this invention are shown in FIG. 1.

V Identification and Full Length Sequencing of the Genes

Figure 2C:
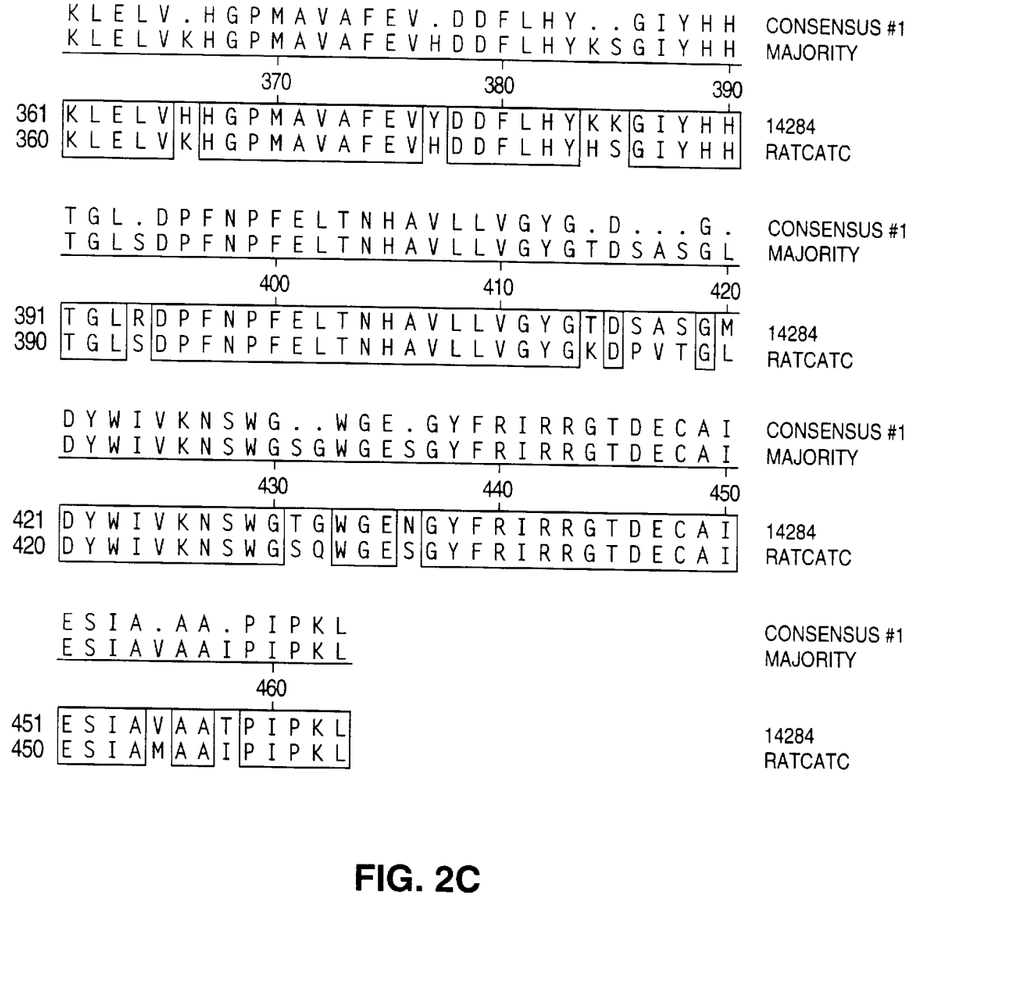
FIG. 2 shows the amino acid alignment of RCP with rat cathepsin C. Alignments shown were produced using the multisequence alignment program of DNASTAR software (DNASTAR Inc, Madison Wis.).

From all of the randomly picked and sequenced clones of the THP-1 library, the rcp sequence was homologous to but clearly different from any known cathepsin C molecule. The complete nucleotide sequence for rcp was translated, and the in-frame translation is shown in FIG. 1. When all three possible predicted translations of the sequence were searched against protein databases such as SwissProt and PIR, no exact matches were found to the possible translations of rcp. FIG. 2 shows the comparison of the RCP amino acid sequence with rat cathepsin C. The substantial regions of homology among these molecules which includes the catalytic triad residues $C_{258}$, $H_{405}$, and $N_{427}$ and NNS glycosylation site$_{276-278}$ common among the cysteine proteases. Hydrophobicity plots for RCP are shown as FIG. 3.

VI Antisense analysis

Knowledge of the correct, complete cDNA sequence of the new cathepsin C gene will enable its use in antisense technology in the investigation of gene function. Oligonucleotides, genomic or cDNA fragments comprising the antisense strand of rcp can be used either in vitro or in vivo to inhibit expression of the protein. Such technology is now well known in the art, and probes can be designed at various locations along the nucleotide sequence. By treatment of cells or whole test animals with such antisense sequences, the gene of interest can effectively be turned off. Frequently, the function of the gene can be ascertained by observing behavior at the cellular, tissue or organismal level (e.g. lethality, loss of differentiated function, changes in morphology, etc.).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of RCP

Expression of rcp may be accomplished by subcloning the cDNAs into appropriate expression vectors and transfecting the vectors into appropriate expression hosts. In this particular case, the cloning vector previously used for the generation of the tissue library also provide for direct expression of the included rcp sequence in E. coli. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The rcp cDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as Saccharomyces cerevisiae, and bacteria such as E. coli. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced RCP can be recovered from the conditioned medium and analyzed using chromatographic methods known in the art.

VIII Isolation of Recombinant RCP

RCP may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen, San Diego Calif.) between the purification domain and the rcp sequence may be useful to facilitate expression of RCP.

IX Production of RCP Specific Antibodies

Two approaches are utilized to raise antibodies to RCP, and each approach is useful for generating either polyclonal or monoclonal antibodies. In one approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

Figure 3:
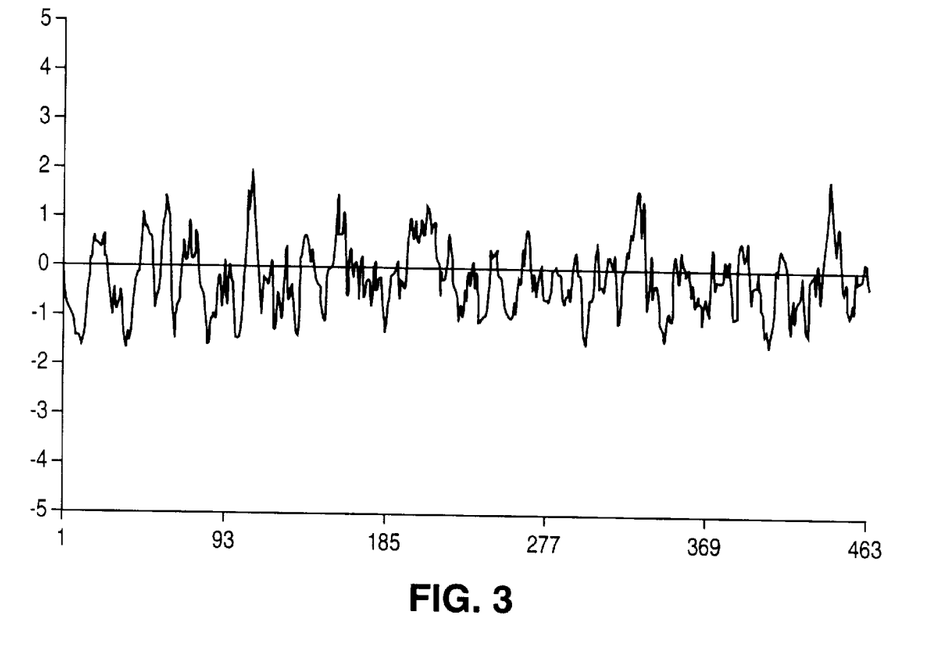
FIG. 3 displays an analysis of RCP hydrophobicity based on the predicted acid amino sequence and composition.

In the second approach, the amino acid sequence of RCP, as deduced from translation of the cDNA, is analyzed to determine regions of high immunogenicity. Oligopeptides comprising appropriate hydrophilic regions, as shown in FIG. 3, are synthesized and used in suitable immunization protocols to raise antibodies. Analysis to select appropriate epitopes is described by Ausubel FM et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled RCP to identify those fusions producing the monoclonal antibody with the desired specificity. In a typical protocol, wells of plates (FAST; Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled RCP, 1 mg/ml. Clones producing antibodies will bind a quantity of labeled RCP which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least 10e8 Me-1, preferably 10e9 to 10e10 or stronger, will typically be made by standard procedures as described in Harlow and Lane (1988) Antibodies: A Laboratory Manual. Cold Spring Harbor Laboratory, Cold Spring Harbor N.Y.; and in Goding (1986) Monoclonal Antibodies: Principles and Practice, Academic Press, New York City, both incorporated herein by reference.

X Diagnostic Test Using RCP Specific Antibodies

Particular RCP antibodies are useful for the diagnosis of prepathologic conditions, and chronic or acute diseases which are characterized by differences in the amount or distribution of RCP. To date, RCP has only been found in the THP-1 library and is thus specific for abnormalities or pathologies which activate monocytes. Diagnostic tests for RCP include methods utilizing the antibody and a label to detect RCP in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277, 437; 4,275,149; and 4,366,241. Also, recombinant immunoglobulins may be produced as shown in U.S. Pat. No. 4,816,567, incorporated herein by reference.

A variety of protocols for measuring soluble or membrane-bound RCP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on RCP is preferred, but a competitive binding assay may be employed. These assays are described, among other places, in Maddox, DE et al (1983, J Exp Med 158:1211).

XI Purification of Native RCP Using Specific Antibodies

Native or recombinant RCP can be purified by immunoaffinity chromatography using antibodies specific for RCP. In general, an immunoaffinity column is constructed by covalently coupling the anti-RCP antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of RCP by preparing a fraction from cells containing RCP in a soluble form. This preparation is derived by solubilization of the whole cell or of a subcellular fraction obtained via differential centrifugation by the addition of detergent or by other methods well known in the art. Alternatively, soluble RCP containing a signal sequence may be secreted in useful quantity into the medium in which the cells are grown.

A soluble RCP-containing preparation is passed over the immunoaffinity column, and the column is washed under conditions that allow the preferential absorbance of cathepsin C (eg, high ionic strength buffers in the presence of detergent). Then, the column is eluted under conditions that disrupt antibody/RCP binding (e.g., a buffer of pH 2–3 or a high concentration of a chaotrope such as urea or thiocyanate ion), and RCP is collected.

XII RCP Activity

The activity of purified or expressed RCP may be tested by mixing a known quantity of the enzyme with a matrix material such as collagen in a biologically acceptable medium and allowing RCP to digest the collagen for a period of time. A zymogram, which consists of a nondenaturing polyacrylamide gel soaked in collagen onto which various concentrations, preferably between 10 and 100 ng/$\mu$l, of RCP are spotted, may be used to demonstrate RCP activity. Staining the gel for protein after digestion will demonstrate those spots in which the concentration of collagen has been reduced (lighter stain) or completely cleared (cf Paech et al (1993) Anal Biochem 208:249–54).

XIII Drug Screening

This invention is particularly useful for screening compounds by using RCP polypeptide or binding fragments thereof in any of a variety of drug screening techniques. The RCP polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between RCP and the agent being tested. Alternatively, one can examine the diminution in complex formation between RCP and its target cell, monocyte, etc. caused by the agent being tested.

Thus, the present invention provides methods of screening for drugs or any other agents which can affect inflammation and disease. These methods comprise contacting such an agent with a RCP polypeptide or fragment thereof and assaying (i) for the presence of a complex between the agent and the RCP polypeptide or fragment, or (ii) for the presence of a complex between the RCP polypeptide or fragment and the cell, by methods well known in the art. In such competitive binding assays, the RCP polypeptide or fragment is typically labeled. After suitable incubation, free RCP polypeptide or fragment is separated from that present in bound form, and the amount of free or uncomplexed label is a measure of the ability of the particular agent to bind to RCP or to interfere with the RCP and agent complex.

Another technique for drug screening provides high throughput screening for compounds having suitable binding affinity to the RCP polypeptide and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with RCP polypeptide and washed. Bound RCP polypeptide is then detected by methods well known in the art. Purified RCP can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding RCP specifically compete with a test compound for binding to RCP polypeptides or fragments thereof. In this manner, the antibodies can be used to detect the presence of any peptide which shares one or more antigenic determinants with RCP.

XIV Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (cf Hodgson J (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous cathepsin C-like molecules or to identify efficient inhibitors. Useful examples of rational drug design may include molecules which have improved activity or stability as shown by Braxton S and Wells J A (1992 Biochemistry 31:7796–7801) or which act as inhibitors, agonists, or antagonists of native peptides as shown by Athauda S B et al (1993 J Biochem 113:742–746), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the RCP amino acid sequence provided herein will provide guidance to those employing computer modeling techniques in place of or in addition to x-ray crystallography.

XV Use and Administration of RCP

Antibodies, inhibitors, or antagonists of RCP (or other treatments for excessive RCP production, hereinafter abbre-viated TEC), can provide different effects when administered therapeutically. TECs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, or antagonist being formulated and the condition to be treated. Characteristics of TEC include solubility of the molecule, half-life and antigenicity/immuno-genicity; these and other characteristics may aid in defining an effective carrier. Native human proteins are preferred as TECs, but organic or synthetic molecules resulting from drug screens may be equally effective in particular situations.

TECs may be delivered by known routes of administration including but not limited to topical creams and gels; transmucosal spray and aerosol, transdermal patch and bandage; injectable, intravenous and lavage formulations; and orally administered liquids and pills, particularly formulated to resist stomach acid and enzymes. The particular formulation, exact dosage, and route of administration will be determined by the attending physician and will vary according to each specific situation.

Such determinations are made by considering multiple variables such as the condition to be treated, the TEC to be administered, and the pharmacokinetic profile of the particular TEC. Additional factors which may be taken into account include disease state (e.g. severity) of the patient, age, weight, gender, diet, time of administration, drug combination, reaction sensitivities, and tolerance/response to therapy. Long acting TEC formulations might be administered every 3 to 4 days, every week, or once every two weeks depending on half-life and clearance rate of the particular TEC.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. It is anticipated that different formulations will be effective for different TECs and that administration targeting the eosinophil may necessitate delivery in a manner different from that to another organ or tissue.

It is contemplated that conditions or diseases of the eosinophil which activate monocytes, macrophages, basophils, eosinophils or other leukocytes may precipitate damage that is treatable with TECs. Monocyte/macrophage disorders may be specifically diagnosed by the tests discussed above, and such testing should be performed in suspected cases of arteriosclerosis, leukemia, systemic lupus erythematosus, osteoporosis, rheumatoid arthritis, toxic shock syndrome and similar physiologic/pathologic problems.

All publications and patents mentioned in the above specification are herein incorporated by reference. The foregoing written specification is considered to be sufficient to enable one skilled in the art to practice the invention. Indeed, various modifications of the above described modes for carrying out the invention which are readily apparent to those skilled in the field of molecular biology or related fields are intended to be within the scope of the following claims.

What is claimed is:

1. An isolated polypeptide comprising the amino acid sequence of SEQ ID NO:2, free of other human proteins.

2. A polypeptide of claim 1, wherein the polypeptide is recombinantly produced.

3. A composition comprising the polypeptide of claim 1 and a suitable aqueous carrier.

4. A method for producing a polypeptide of claim 1, comprising a) culturing a host cell transformed with an expression vector comprising a DNA molecule encoding a polypeptide having the amino acid sequence of SEQ ID NO:2 under conditions suitable for expression of the polypeptide; and b) recovering the polypeptide from the cell culture.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 1389 base pairs
       (B) TYPE: nucleic acid
       (C) STRANDEDNESS: single
       (D) TOPOLOGY: linear (ii) MOLECULE TYPE: cDNA (vii) IMMEDIATE SOURCE:
       (A) LIBRARY: THP-1
       (B) CLONE: 14284

(xi) SEQUENCE DESCRIPTION: SEQ ID NO:1:

```
ATGGGTGCTG GGCCCTCCTT GCTGCTCGCC GCCCTCCTGC TGCTTCTCTC CGGCGACGGC      60
GCCGTGCGCT GCGACACACC TGCCAACTGC ACCTATCTTG ACCTGCTGGG CACCTGGGTC     120
TTCCAGGTGG GCTCCAGCGG TTCCCAGCGC GATGTCAACT GCTCGGTTAT GGGACCACAA     180
GAAAAAAAG TAGTGGTGTA CCTTCAGAAG CTGGATACAG CATATGATGA CCTTGGCAAT      240
TCTGGCCATT TCACCATCAT TTACAACCAA GGCTTTGAGA TTGTGTTGAA TGACTACAAG     300
TGGTTTGCCT TTTTTAAGTA TAAAGAAGAG GGCAGCAAGG TGACCACTTA CTGCAACGAG     360
ACAATGACTG GGTGGGTGCA TGATGTGTTG GGCCGGAACT GGGCTTGTTT CACCGGAAAG     420
AAGGTGGGAA CTGCCTCTGA GAATGTGTAT GTCAACACAG CACACCTTAA GAATTCTCAG     480
GAAAAGTATT CTAATAGGCT CTACAAGTAT GATCACAACT TTGTGAAAGC TATCAATGCC     540
ATTCAGAAGT CTTGGACTGC AACTACATAC ATGGAATATG AGACTCTTAC CCTGGGAGAT     600
ATGATTAGGA GAAGTGGTGG CCACAGTCGA AAAATCCCAA GGCCCAAACC TGCACCACTG     660
ACTGCTGAAA TACAGCAAAA GATTTTGCAT TTGCCAACAT CTTGGGACTG GAGAAATGTT     720
CATGGTATCA ATTTTGTCAG TCCTGTTCGA AACCAAGCAT CCTGTGGCAG CTGCTACTCA     780
TTTGCTTCTA TGGGTATGCT AGAAGCGAGA ATCCGTATAC TAACCAACAA TTCTCAGACC     840
CCAATCCTAA GCCCTCAGGA GGTTGTGTCT TGTAGCCAGT ATGCTCAAGG CTGTGAAGGC     900
GGCTTCCCAT ACCTTATTGC AGGAAAGTAC GCCCAAGATT TTGGGCTGGT GGAAGAAGCT     960
TGCTTCCCCT ACACAGGCAC TGATTCTCCA TGCAAAATGA AGGAAGACTG CTTTCGTTAT    1020
TACTCCTCTG AGTACCACTA TGTAGGAGGT TTCTATGGAG GCTGCAATGA AGCCCTGATG    1080
AAGCTTGAGT TGGTCCATCA TGGGCCCATG GCAGTTGCTT TTGAAGTATA TGATGACTTC    1140
CTCCACTACA AAAGGGGAT CTACCACCAC ACTGGTCTAA GAGACCCTTT CAACCCCTTT     1200
GAGCTGACTA ATCATGCTGT TCTGCTTGTG GGCTATGGCA CTGACTCAGC CTCTGGGATG    1260
GATTACTGGA TTGTTAAAAA CAGCTGGGGC ACCGGCTGGG GTGAGAATGG CTACTTCCGG    1320
ATCCGCAGAG GAACTGATGA GTGTGCAATT GAGAGCATAG CAGTGGCAGC CACACCAATT    1380
CCTAAATTG                                                            1389
```

(2) INFORMATION FOR SEQ ID NO:2:

(i) SEQUENCE CHARACTERISTICS:
       (A) LENGTH: 463 amino acids
       (B) TYPE: amino acid
       (D) TOPOLOGY: linear (ii) MOLECULE TYPE: protein (xi) SEQUENCE DESCRIPTION: SEQ ID NO:2:

```
Met Gly Ala Gly Pro Ser Leu Leu Leu Ala Ala Leu Leu Leu Leu
 1               5                  10                  15

Ser Gly Asp Gly Ala Val Arg Cys Asp Thr Pro Ala Asn Cys Thr Tyr
            20                  25                  30

Leu Asp Leu Leu Gly Thr Trp Val Phe Gln Val Gly Ser Ser Gly Ser
        35                  40                  45

Gln Arg Asp Val Asn Cys Ser Val Met Gly Pro Gln Glu Lys Lys Val
    50                  55                  60

Val Val Tyr Leu Gln Lys Leu Asp Thr Ala Tyr Asp Asp Leu Gly Asn
65                  70                  75                  80

Ser Gly His Phe Thr Ile Ile Tyr Asn Gln Gly Phe Glu Ile Val Leu
                85                  90                  95

Asn Asp Tyr Lys Trp Phe Ala Phe Phe Lys Tyr Lys Glu Glu Gly Ser
            100                 105                 110

Lys Val Thr Thr Tyr Cys Asn Glu Thr Met Thr Gly Trp Val His Asp
        115                 120                 125

Val Leu Gly Arg Asn Trp Ala Cys Phe Thr Gly Lys Lys Val Gly Thr
    130                 135                 140

Ala Ser Glu Asn Val Tyr Val Asn Thr Ala His Leu Lys Asn Ser Gln
145                 150                 155                 160

Glu Lys Tyr Ser Asn Arg Leu Tyr Lys Tyr Asp His Asn Phe Val Lys
                165                 170                 175

Ala Ile Asn Ala Ile Gln Lys Ser Trp Thr Ala Thr Thr Tyr Met Glu
            180                 185                 190

Tyr Glu Thr Leu Thr Leu Gly Asp Met Ile Arg Arg Ser Gly Gly His
        195                 200                 205

Ser Arg Lys Ile Pro Arg Pro Lys Pro Ala Pro Leu Thr Ala Glu Ile
    210                 215                 220

Gln Gln Lys Ile Leu His Leu Pro Thr Ser Trp Asp Trp Arg Asn Val
225                 230                 235                 240

His Gly Ile Asn Phe Val Ser Pro Val Arg Asn Gln Ala Ser Cys Gly
                245                 250                 255

Ser Cys Tyr Ser Phe Ala Ser Met Gly Met Leu Glu Ala Arg Ile Arg
            260                 265                 270

Ile Leu Thr Asn Asn Ser Gln Thr Pro Ile Leu Ser Pro Gln Glu Val
        275                 280                 285

Val Ser Cys Ser Gln Tyr Ala Gln Gly Cys Glu Gly Gly Phe Pro Tyr
    290                 295                 300

Leu Ile Ala Gly Lys Tyr Ala Gln Asp Phe Gly Leu Val Glu Glu Ala
305                 310                 315                 320

Cys Phe Pro Tyr Thr Gly Thr Asp Ser Pro Cys Lys Met Lys Glu Asp
                325                 330                 335

Cys Phe Arg Tyr Tyr Ser Ser Glu Tyr His Tyr Val Gly Gly Phe Tyr
            340                 345                 350

Gly Gly Cys Asn Glu Ala Leu Met Lys Leu Glu Leu Val His His Gly
        355                 360                 365

Pro Met Ala Val Ala Phe Glu Val Tyr Asp Asp Phe Leu His Tyr Lys
    370                 375                 380

Lys Gly Ile Tyr His His Thr Gly Leu Arg Asp Pro Phe Asn Pro Phe
385                 390                 395                 400
```

-continued

```
Glu Leu Thr Asn His Ala Val Leu Leu Val Gly Tyr Gly Thr Asp Ser
                405                 410                 415

Ala Ser Gly Met Asp Tyr Trp Ile Val Lys Asn Ser Trp Gly Thr Gly
            420                 425                 430

Trp Gly Glu Asn Gly Tyr Phe Arg Ile Arg Arg Gly Thr Asp Glu Cys
        435                 440                 445

Ala Ile Glu Ser Ile Ala Val Ala Ala Thr Pro Ile Pro Lys Leu
    450                 455                 460
```